United States Patent [19]

Pugh

[11] Patent Number: 4,795,425
[45] Date of Patent: Jan. 3, 1989

[54] SPERMICIDAL CONDOM

[75] Inventor: Bradley L. Pugh, Midland City, Ala.

[73] Assignee: Ansell Incorporated, Dothan, Ala.

[21] Appl. No.: 803,413

[22] Filed: Dec. 2, 1985

Related U.S. Application Data

[63] Continuation-in-part of Ser. No. 741,202, Jun. 4, 1985, abandoned, which is a continuation of Ser. No. 595,639, Apr. 2, 1984, abandoned, which is a continuation of Ser. No. 318,773, Nov. 6, 1981, abandoned.

[51] Int. Cl.$^4$ .............................................. A61F 5/44
[52] U.S. Cl. ..................................... 128/844; 604/349
[58] Field of Search ........................... 128/132 R, 127; 604/349–353, 330; 424/44, 45

[56] References Cited

U.S. PATENT DOCUMENTS

| | | | |
|---|---|---|---|
| Re. 29,102 | 1/1977 | Scherm | 424/44 |
| D. 246,119 | 10/1977 | Okamoto | 604/349 |
| 2,904,041 | 9/1959 | Brown | 128/132 R |
| 3,282,414 | 11/1966 | Penska | 128/132 R |
| 3,363,624 | 1/1968 | Fishman | 128/132 R |
| 3,826,828 | 7/1974 | Morel | 128/132 R |
| 4,004,591 | 1/1977 | Freimark | 604/330 |
| 4,187,286 | 2/1980 | Marcus | 514/629 |
| 4,332,243 | 6/1982 | Gutnick | 128/132 R |
| 4,415,548 | 11/1983 | Reddy | 128/132 R |

Primary Examiner—C. Fred Rosenbaum
Assistant Examiner—Mario Costantino
Attorney, Agent, or Firm—Ladas & Parry

[57] ABSTRACT

A spermicidal contraceptive sheath and method of manufacture are disclosed. The sheath has a first spermicide-containing semi-solid inside the sheath at the closed end thereof. A spermicide-containing lubricant is provided at least on the outside surface of the sheath. A dose of spermicide is automatically provided both on the outside of the sheath and on the inside. If the sheath ruptures, a double dosage of spermicide is available to provide an extra measure of contraceptive effectiveness.

17 Claims, 1 Drawing Sheet

SPERMICIDAL CONDOM

BACKGROUND OF THE INVENTION

1. Field of the Invention

The present application is a continuation in part of our copending application Ser. No. 741202 filed on June 4, 1985 (now abandoned) which is in turn a continuation of application Ser. No. 595639 filed Apr. 2, 1984 (now abandoned) which is itself a continuation of application Ser. No. 318773 filed Nov. 6, 1981 (now abandoned).

The present invention pertains to condoms and, more particularly, to a condom or contraceptive sheath that is provided with spermicide-containing lubricant to provide an extra measure of effectiveness against conception, and a method of manufacture.

2. Description of the Prior Art

Contraceptive devices such as condoms comprising contraceptive sheaths for insertion upon the male organ have long been used as a means for preventing conception. The sheaths are typically made of latex rubber, are generally tubular, and have a closed end and an open end.

Conventional contraceptive sheaths are often provided with lubricants comprising a synthetic polyether, such as polyethylene glycol.

It has long been a problem with conventional contraceptive sheaths that they occasionally fail to prevent conception. The failure frequently results from a rupture of the thin wall of the sheath, usually at the tip which is subjected to stresses such as stretching. Failure also occurs from the tendency of improperly fitted sheaths to roll up during and after use.

An attempt to overcome the foregoing problems is disclosed in commonly assigned British Patent No. 1,142,443 which discloses a sheath having a constricted portion spaced from the closed end to form an improved fluid tight seal with the male organ. However, no means of preventing conception is disclosed for instances where the sheath ruptures or the sheath nevertheless rolls up.

Another attempt at solving the foregoing problems is disclosed in British Patent No. 1,268,637 which discloses a contraceptive sheath which has polyether applied thereto as a lubricant. The polyether can be applied in aqueous solution or in combination with a spermicide to render the sheath more contraceptively efficient. It is a disadvantage of this arrangement that an effective amount of spermicide is not provided inside the sheath at the tip thereof. Accordingly, when the need for the spermicide arises, the sheath can fail to kill the sperm, as is required.

Other attempts to overcome these problems have been made by using contraceptive sheaths in conjunction with spermicide foams, jellies, or suppositories, thereby relying on two separate methods of contraception. The use of the spermicide in this manner has the disadvantage of inconvenience in that the male and female must have the forethought and planning not only to have both the spermicidal preparation and sheaths on hand, but also to insert the spermicidal preparation at some predetermined, recommended time interval prior to intercourse.

SUMMARY OF THE INVENTION

The foregoing disadvantages of the prior art are overcome in accordance with the present invention which provides a spermicidal contraceptive sheath and a method of manufacture.

Recent publications have shown that spermicides such as Nonoxynol 9 not only have contraceptive effects but are also effective in controlling sexually transmitted diseases such as gonorrhoea, chlamydia herpes and the AIDS virus. The present invention provides an effective means for delivering spermicide at the site where it is most effective to combat said sexually transmitted diseases.

The contraceptive sheath has a closed end and an open end, and has an outside surface and an inside surface. A spermicide-containing semi solid composition is provided on the inside surface of the closed end of the sheath. The composition has a sufficiently high interfacial surface tension to retain the ointment on the inside surface of the sheath.

A spermicide-containing lubricant is provided on the outside surface of the sheath. A first dosage of spermicide is thereby available within the sheath and a second dosage of spermicide is available outside the sheath thereby to provide a more effective arrangement for preventing conception.

A method of manufacturing a spermicidal contraceptive sheath in accordance with the present invention comprises the steps of providing a contraceptive sheath having a closed end and an open end, an outside surface and an inside surface, applying a first spermicide-containing semi solid material on the inside surface of the closed end of the sheath, applying a spermicide-containing lubricant on the sheath, spreading the lubricant about the outside surface of the sheath, thereby providing one dosage of spermicide within the sheath and another dosage of spermicide outside the sheath.

It is a feature of the present invention that a dose of spermicide is automatically available both on the outside of the condom and on the inside. In the event the condom should rupture, a double dosage of spermicide is available due to the combination of the dosage inside the condom and the dosage outside. If the condom should accidentally come off, or if there is a rupture subsequent to ejaculation, the spermicide would already have killed substantially all of the sperm inside the condom. Accordingly, an extra measure of contraceptive effectiveness and protection is available with the present invention. In the event that the condom does not rupture or become accidentally removed, then each partner is only exposed to a single dose of the spermicide.

DETAILED DESCRIPTION OF THE PREFERRED EMBODIMENT

Figure 1:
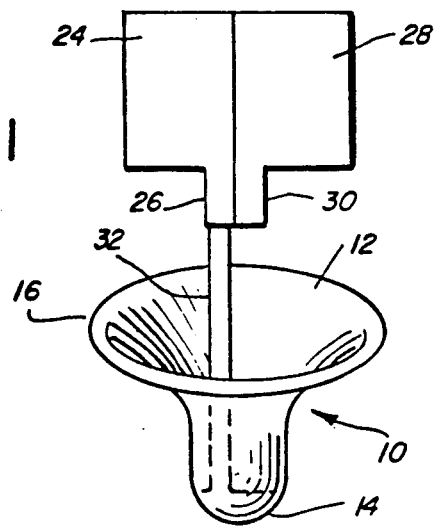
FIG. 1 is a schematic illustration of a spermicidal contraceptive sheath in accordance with the present invention, in which a composition is being applied to the sheath.

While this invention is susceptible of embodiment in many different forms, there is shown in the drawing and will herein be described in detail one specific embodiment, with the understanding that the present disclosure is to be considered as an exemplification of the principles of the present invention, and is not intended to limit the invention to the embodiment illustrated.

Figure 2:
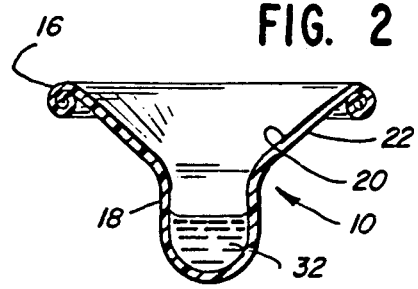
FIG. 2 is a cross-sectional view of the sheath after the composition is fully received therein.

Referring to the drawing, FIGS. 1 and 2 show a conventional contraceptive device or sheath 10. The sheath comprises a condom or prophylactic device which is made of any suitable material, such as latex rubber, in the form of a flexible and resilient hollow tubular sheath.

The sheath 10 has an upper open end 12 (FIG. 1) for insertion of the male organ therein and a sloping, lower closed end 14 which is generally hemispherical and comprises a nipple that acts as a barrier against the seepage of fluids from the discharge zone of the organ disposed in the interior of the sheath.

The sheath also includes an elastic peripheral portion 16 which defines the open end 12 of the sheath. The elastic portion engages the body portion of the organ when the device is in its operative position so as to provide a seal against the flow of fluid into and out of the interior of the device. The elastic portion 16 provides a band upon which the wall 18 of the device is rolled when the device is not in use. In the position shown in the illustrated embodiment, a major portion of the wall 18 of the sheath is rolled about the elastic portion 16.

The sheath also includes an inside surface 20 and an outside surface 22, as illustrated in FIG. 2.

Referring again to FIG. 1, a pair of extruders are shown for metering predetermined quantities of spermicide-containing compositions to the contraceptive sheath 10. Shown schematically are a first extruder 24 having a nozzle 26 and a second extruder 28 having a nozzle 30.

A first spermicide-containing lubricant is provided in the extruder 24, and a metered quantity is applied to the inside surface 20 of the closed end 14 of the sheath 10. During the manufacturing process, the sheath 10 is held upright as shown in FIG. 1, and the predetermined quantity of the first lubricant 32 can be fed to the closed end of the sheath by means of gravity, with the nozzle 26 being positioned directly above the closed end 14 of the sheath.

The spermicide-containing composition is applied to the sheath in the form of a semi-solid, such as a cream.

The composition 32 is disposed substantially entirely within the closed end 14 of the sheath. The material therefore has a sufficiently high coefficient of friction to retain it on the inside surface of the closed end of the sheath, thereby to prevent migration of the material by means of capillary action.

Figure 3:
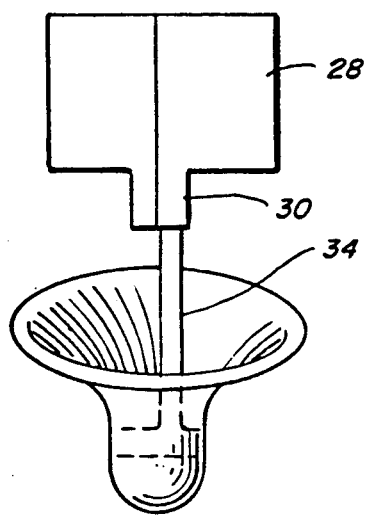
FIG. 3 is a schematic illustration of the sheath while a lubricant is applied thereto.
Figure 4:
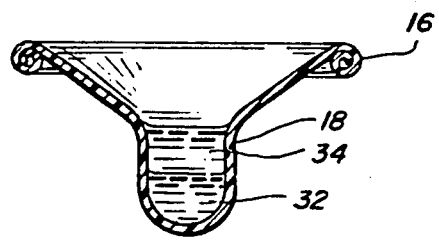
FIG. 4 is a cross-sectional view of the sheath after the lubricant is fully received therein.

Referring to FIG. 3, a spermicide-containing lubricant 34 is applied to the sheath after the first spermicide-containing composition is fully received within the sheath. The lubricant 34 is provided within the extruder 28, and a metered quantity is fed to the sheath by means of the nozzle 30. The nozzle 30 is positioned directly above the sheath, and the lubricant 34 is applied on top of the first spermicide-containing composition by way of gravity. Immediately after the lubricant 34 is applied to the sheath, it is disposed within the closed end 14 of the sheath, above the first spermicide-containing composition 32, as depicted in FIG. 4.

It is desired to have the lubricant provided on the outside surface of the sheath 10, so that the dosage of spermicide provided by the lubricant is available for the female. Accordingly, the lubricant may be applied directly to the outside surface of the sheath, if desired. Alternatively, the lubricant 34 can be applied to the inside of the sheath, as shown in FIG. 4, and the lubricant 34 is of the type that has a sufficiently low coefficient of friction to spread by means of capillary action to both the inside surface 20 and outside surface 22 of the sheath. The spreading will take place even while the sheath is rolled about the peripheral portion 16. The migration of the lubricant along the inside surface and the outside surface will typically occur during a twenty-four to forty-eight hour period.

Figure 5:
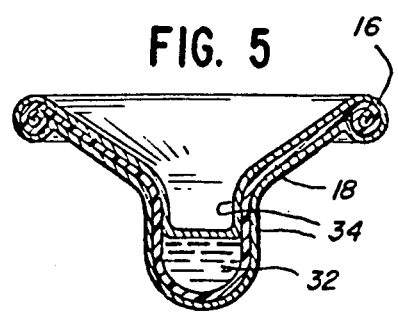
FIG. 5 is a cross-sectional view of the sheath after the passage of time which enables the lubricant to spread along the surface of the sheath.

The final product is shown in FIG. 5. The first spermicide-containing composition 32 is disposed substantially entirely within the closed end 14 of the sheath, and the lubricant 34 is disposed about the entire outside surface 22 of the sheath, and the entire inside surface 20 with the exception of the portion that is already covered by the first spermicide-containing composition. In accordance with the foregoing, the sheath 10 has a relatively large first dosage of spermicide contained within the closed end 14 of the sheath, which is the tip where most ruptures occur. As a result, sperm that is released from the condom would substantially all be killed by the spermicide which is provided in that location.

A second dose of spermicide is provided on the outside surface of the sheath, which is received by the woman. Thus, if the sheath ruptures, a double quantity of spermicide is available--one dose from the inside and a second dose from the outside. Accordingly, an extra measure of contraceptive effectiveness is available over a standard condom, while exposing each person to only a single dose of spermicide if no rupture occurs.

The first spermicide-containing composition 32 preferably comprises an ointment or cream which is in semi-solid form. By way of example, the composition 32 may comprise a mixture of 30% by volume of polyethylene glycol 3350, 63.4% by volume polyethylene glycol 400, and 6.6% by volume of the spermicide known as Nonoxynol-9 which has the chemical name nonylphenoxypolyethoxyethanol. The foregoing materials are available from Union Carbide Corporation under the trade names Carbowax 3350, Carbowax 400, and Tergitol NP-9, respectively. The foregoing mixture provides a suitable ointment form for application of the composition 32. Such compositions typically melt in the range 113°-127° F.

The spermicide may range from 2-10% by volume of the mixture of the first composition, preferably between about 6.1% and 7.1% by volume, and most preferably about 6.6% by volume. The quantity of the first composition 32 that is applied to the sheath ranges from about 0.3 gram to about 0.6 gram, preferably between 0.35 gram and 0.55 gram, and most preferably about 0.45 gram.

By way of example, the lubricant 34 may be a silicone fluid comprising dimethylpolysiloxane fluid containing a predetermined quantity of a spermicide such as Nonoxynol-9. The volume of Nonoxynol may range from 2-10%, preferably between about 6.1% and 7.1%, and most preferably about 6.6%. The quantity of the lubricant may range from 0.3 to 0.6 gram, preferably between about 0.35 gram and 0.55 gram, and most preferably about 0.45 gram.

In order for the lubricant to spread about the surfaces of the sheath, it has a viscosity between about 50–500 centistokes, preferably about 200 centistokes.

When the preferred range of between about 6.1% and 7.1% by volume of the spermicide-containing materials are used, with the lubricants each being in the preferred range of 0.35 gram to 0.55 gam, the quantity of spermicide in each spermicide-containing material ranges from about 21.35 mg to about 39.05 mg. The spermicide becomes diluted by vaginal fluids. Accordingly, the foregoing range for the amount of spermicide is greater than the quantity required for killing the sperm, and it has been found that effectiveness can be obtained with lesser amounts of spermicide, such as 10 mg.

An advantage in providing spermicide on the outside surface of the sheath is that the spermicide is spread about the vagina during intercourse and is available to kill sperm should the sheath rupture or otherwise fail. An extra measure of effectiveness is thereby provided.

The primary means for killing sperm, however, is by providing a relatively large quantity of spermicide at the closed end of the sheath, where the spermicide is available to directly contact the sperm when it originally is provided by the male organ. In many instances, the first spermicide-containing composition inside the sheath is all that is required to prevent conception if the sheath ruptures or otherwise fails.

From the foregoing, it will be observed that numerous variations and modifications may be affected without departing from the true spirit and scope of the novel concept of the invention. It is to be understood that no limitation with respect to the specified device illustrated herein and the method described herein is intended or should be inferred. It is, of course, intended to cover by the appended claims all such modifications as fall within the scope of the claims.

I claim:

1. A spermicidal contraceptive sheath, comprising
   a contraceptive sheath having a closed end and an open end, said sheath having an outside surface and an inside surface,
   a first spermicide-containing composition provided on said inside surface of the closed end of said sheath, said first composition being in use retained at the closed end of the sheath by virtue of said composition having the properties of (1) high interfacial surface tension with the inside surface of the sheath and (2) a melting point in the range 113°–127° F. interfacial surface tension to retain said first composition in use at its position at the closed end of the sheath, and
   a spermicide-containing lubricant provided on said outside surface of said sheath,
   whereby a first dosage of spermicide is available within said sheath and a second dosage of spermicide is available outside said sheath.

2. A contraceptive sheath as defined in claim 1, wherein said first composition is in a semi-solid form.

3. A contraceptive sheath as defined in claim 2, wherein said first composition is contained substantially within said closed end of said sheath.

4. A contraceptive sheath as defined in claim 1, wherein said lubricant has a sufficiently low interfacial surface tension to spread by means of capillary action to both said inside surface and said outside surface of said sheath.

5. A contraceptive sheath as defined in claim 1, wherein said first composition is a solid or semi-solid comprising polyethylene glycol containing between 6.1% and 7.1% by volume of nonylphenoxypolyethoxyethanol.

6. A contraceptive sheath as defined in claim 5, wherein between about 0.35 gram and about 0.55 gram of said first composition is provided in said sheath.

7. A contraceptive sheath as defined in claim 6, wherein said first composition is contained substantially within said closed end of said sheath.

8. A contraceptive sheath as defined in claim 1, wherein said lubricant comprises a silicone fluid containing between about 6.1% and about 7.1% by volume of nonylphenoxypolyethoxyethanol.

9. A contraceptive sheath as defined in claim 8, wherein said silicone liquid comprises dimethylpolysiloxane.

10. A contraceptive sheath as defined in claim 9, wherein between about 0.35 gram and about 0.55 gram of said lubricant is provided on said sheath.

11. A spermicidal contraceptive sheath as claimed in claim 1, wherein said semi-solid spermicide-containing composition is disposed in a nipple at the closed end of said sheath.

12. A spermicidal contraceptive sheath as claimed in claim 1, wherein said semi-solid spermicide-containing composition comprises a mixture of about 30% of volume of polyethylene glycol 3350, about 63.4% by volume polyethylene glycol 400 and about 6.6% by volume nonylphenoxypolyethoxy ethanol.

13. A method of manufacturing a spermicidal contraceptive sheath, comprising the steps of
   providing a contraceptive sheath having a closed end and an open end, an outside surface and an inside surface,
   applying a first spermicide-containing semi-solid composition having a melting point in the range 113°–127° F. on the inside surface of the closed end of the sheath,
   applying a spermicide-containing lubricant on said sheath,
   spreading said second lubricant about the outside surface of said sheath,
   thereby providing one dosage of spermicide within said sheath and another dosage of spermicide outside said sheath.

14. A method of preventing the transmission of sexually transmitted diseases which comprises enclosing the penis of a male participating in sexual intercourse with a contraceptive sheath having a closed end and an open end, said sheath having an outside surface and an inside surface, there being disposed on the inside surface thereof a nonylphenoxypolyethoxy ethanol-containing composition having a melting point in the range 113°–127° F. and an interfacial surface tension with the inside of the sheath that is sufficiently high to retain said composition in use at its position and the closed end of the sheath.

15. A method according to claim 14, wherein the contraceptive sheath employed has a nonylphenoxypolyethoxy ethanol-containing lubricant on outside surface of said sheath.

16. A method according to claim 15, wherein the contraceptive sheath employed is one wherein said lubricant is a silicone fluid containing between about 6.1% and about 7.1% by volume of nonylphenoxypolyethoxy ethanol.

17. A method according to claim 14, wherein the contraceptive sheath employed in one wherein said nonylphenoxypolyethoxy ethanol-containing composition on the inside of the sheath is a solid or semi-solid composition comprising about 30% by volume of polyethylene glycol 3350, about 63.4% by volume polyethylene glycol 400 and about 6.6% by volume nonylphenoxypolyethoxy ethanol.

* * * * *